US009848798B2

(12) United States Patent
Candidus et al.

(10) Patent No.: US 9,848,798 B2
(45) Date of Patent: Dec. 26, 2017

(54) POSITIONING APPARATUS

(71) Applicants: Yvonne Candidus, Fürth (DE); Daniel Driemel, Oederan (DE); Hubertus Fischer, Bamberg (DE); Wolfgang Kraus, Fürth (DE); Thomas Kundner, Buckenhof (DE); Martin Zigann, Brunn (DE); Stephan Zink, Erlangen (DE)

(72) Inventors: Yvonne Candidus, Fürth (DE); Daniel Driemel, Oederan (DE); Hubertus Fischer, Bamberg (DE); Wolfgang Kraus, Fürth (DE); Thomas Kundner, Buckenhof (DE); Martin Zigann, Brunn (DE); Stephan Zink, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/476,428

(22) Filed: Sep. 3, 2014

(65) Prior Publication Data
US 2015/0059093 A1    Mar. 5, 2015

(30) Foreign Application Priority Data
Sep. 3, 2013 (DE) ........................ 10 2013 217 533

(51) Int. Cl.
*A61B 6/04* (2006.01)
*A61B 5/055* (2006.01)

(52) U.S. Cl.
CPC .......... *A61B 5/0555* (2013.01); *A61B 6/0407* (2013.01)

(58) Field of Classification Search
CPC ..... A61B 5/704; A61B 6/0407; A61B 6/0421; A61B 6/0442; A61B 5/0555; A61G 7/015;
(Continued)

(56) References Cited

U.S. PATENT DOCUMENTS 3,584,321 A * 6/1971 Buchanan .............. A61G 13/02
5/601
5,613,254 A * 3/1997 Clayman .............. A61B 6/0442
5/172
(Continued)

FOREIGN PATENT DOCUMENTS

| DE | 20009909 U1 | 8/2000 |
| DE | 69527178 T2 | 1/2003 |
| WO | WO0191642 A1 | 12/2001 |

OTHER PUBLICATIONS

German Office Action for German Application No. 10 2013 217 533.7, dated May 13, 2014, with English Translation.

*Primary Examiner* — Nicholas Polito
(74) *Attorney, Agent, or Firm* — Lempia Summerfield Katz LLC

(57) ABSTRACT

A positioning apparatus configured to actively assist the support, positioning, or support and positioning of a patient on a patient support apparatus is provided. The positioning apparatus includes a sliding bearing unit to allow the positioning apparatus to be supported in a movable manner on the patient support apparatus, and a bearing unit with at least two bearing regions. At least a first of the at least two bearing regions is configured to support and/or provide support on the patient support apparatus, and at least a second of the at least two bearing regions is configured to assist the positioning of the patient.

22 Claims, 2 Drawing Sheets

(58) Field of Classification Search
CPC .... A61G 7/018; A61G 13/08; A61G 13/0018; A61G 13/02; A61G 13/04; A61G 13/122
See application file for complete search history.

(56) References Cited

U.S. PATENT DOCUMENTS

| | | | | |
|---|---|---|---|---|
| 5,678,263 | A * | 10/1997 | Berthe | A61B 5/221 5/600 |
| 5,926,876 | A * | 7/1999 | Haigh | A61G 13/12 5/616 |
| 6,138,302 | A * | 10/2000 | Sashin | A61B 6/0421 5/600 |
| 6,442,777 | B1 * | 9/2002 | Pauli | A61B 6/032 5/601 |
| 7,669,262 | B2 * | 3/2010 | Skripps | A61G 13/0054 5/621 |
| 2007/0277317 | A1 * | 12/2007 | Ferko | A61G 7/015 5/620 |
| 2010/0329414 | A1 * | 12/2010 | Zhu | A61N 5/10 378/4 |

* cited by examiner

POSITIONING APPARATUS

This application claims the benefit of DE 10 2013 217 533.7, filed on Sep. 3, 2013, which is hereby incorporated by reference in its entirety.

BACKGROUND

The support and/or positioning of patients (e.g., physically impaired patients) on a medical patient support apparatus requires major expenditure of force on the part of medical operators, particularly physicians or medical technical assistants. For example, the change of support and/or repositioning from a sitting position to a horizontal position and vice versa imposes a major strain on medical operators.

SUMMARY AND DESCRIPTION

The scope of the present invention is defined solely by the appended claims and is not affected to any degree by the statements within this summary.

The present embodiments may obviate one or more of the drawbacks or limitations in the related art. For example, support and/or a change of support for a patient on a patient support apparatus is assisted and/or facilitated.

One or more of the present embodiments are based on a positioning apparatus configured, for example, to actively assist the support and/or positioning of a patient on a patient support apparatus. The positioning apparatus includes a sliding bearing unit to allow the positioning apparatus to be supported in a movable manner on the patient support apparatus, and a bearing unit with at least two bearing regions. At least a first of the at least two bearing regions is configured to support and/or provide support on the patient support apparatus, and at least a second of the at least two bearing regions is configured to assist the positioning of the patient. The positioning apparatus (e.g., the at least one second bearing region of the bearing unit) may advantageously be used to actively assist the repositioning and/or a change of support for the patient (e.g., from a sitting position to a horizontal position of the patient or from a horizontal position to a sitting position of the patient) on a patient support apparatus, thereby minimizing the force expenditure on the part of a medical operator during the change of support and/or repositioning of the patient. The sliding bearing unit may also be used to achieve advantageous positioning of the positioning apparatus on the patient support apparatus (e.g., such that the positioning apparatus is tailored to the size of the patient). The at least two bearing regions of the bearing unit may each be configured to support and/or hold the patient, with, however, at least a first of the bearing regions being configured for positioning on the patient support apparatus (e.g., a table of the patient support apparatus), and at least a second of the bearing regions being configured to assist actively during a change of support and/or repositioning of the patient. The at least two bearing regions of the bearing unit also allow an advantageous stability of the positioning apparatus to be achieved during a change of support and/or repositioning of the patient. In one embodiment, an existing patient support apparatus may thus be retrofitted in a particularly economical manner using the positioning apparatus.

In one embodiment, the sliding bearing unit has at least one sliding bearing element that is arranged on the at least one first bearing region. This allows the positioning apparatus to be securely supported on a patient support apparatus in a particularly simple manner, in that the at least one sliding bearing element is arranged on the bearing region provided for the support and/or positioning of the positioning apparatus on a patient support apparatus. The at least one sliding bearing element of the positioning apparatus may, for example, be configured in the same way as a sliding bearing element of the patient support apparatus, so that, for example, movement of the positioning apparatus may be provided in the direction of a longitudinal extension of the patient support apparatus on the patient support apparatus.

If the at least one first bearing region has at least one strip element, and the at least one sliding bearing element is arranged on the at least one strip element, a particularly compact positioning apparatus may be provided. The positioning apparatus may include at least two strip elements. Each of the at least two strip elements has a sliding bearing element of the sliding bearing unit. The at least one sliding bearing element may, for example, be arranged on end regions of the strip elements or may be arranged on the strip elements in the manner of a rail. A rail-type sliding bearing element, for example, extends in the direction of a longitudinal extension of the strip elements.

In a further embodiment, the at least one first bearing region has at least one securing element, allowing advantageous securing of the positioning apparatus to be achieved to prevent a change of position of the positioning apparatus in at least one direction on a patient support apparatus. The securing element advantageously secures a position of the positioning apparatus on the patient support apparatus in two different directions and at the same time allows movement of the positioning apparatus on the patient support apparatus in a movement direction (e.g., a sliding direction) of the positioning apparatus. The securing element may also be configured as a single piece and/or as a single part with a sliding bearing element.

A particularly stable and secure bearing surface for supporting and/or positioning the patient may advantageously be provided if at least one of the bearing regions has two strip elements, between which a bearing element of the bearing region is arranged to support the patient. The at least two strip elements may be arranged on different (e.g., opposing) sides of the bearing region. The strip elements may, for example, be formed by profile strip elements and/or a further configuration.

In one embodiment, at least one of the bearing regions has at least one bearing element with a thickness of maximum 1 cm. The bearing element may have a thickness of maximum 5 mm, maximum 2.5 mm, or maximum 1 mm. The configuration advantageously allows an essentially smooth transition to be achieved between the at least one bearing element and, for example, a support surface of a table of the patient support apparatus. The positioning apparatus may be configured such that each of the bearing regions of the positioning apparatus has at least one bearing element in each instance. In one embodiment, the at least two bearing regions may have a common bearing element. The thin configuration of the positioning apparatus (e.g., the bearing element) also allows the distance between the patient and a high-frequency receive unit for a magnetic resonance examination integrated within the table to be minimized, so that unwanted signal attenuation as a result of the positioning apparatus is advantageously prevented.

In a further embodiment, at least one of the bearing regions has at least one bearing element that includes a flat textile structure. The flat textile structure of the at least one bearing element allows advantageous tailoring of the at least one bearing element to a patient (e.g., to a contour and/or anatomy of a leg region of the patient) to be achieved. This embodiment also allows a particularly thin and light bearing element to be provided to support and/or position the patient. In this context, a flat textile structure refers, for example, to a fabric (e.g., a material and/or a cloth and/or a synthetic fabric, and/or a mesh, and/or a non-woven fabric and/or further flat textile structures). If the flat textile structure is also formed by a material and/or a cloth, the material and/or cloth may rest on the table as a result of loading by the patient and yielding on the part of the material and/or cloth. When the patient is supported and/or positioned on the bearing unit, this results in the fixing of the position of the positioning apparatus in relation to the patient support apparatus, in that the direct contact between the bearing element and the support surface of the table provides that a friction force acts between the bearing element and the support surface of the table, thereby allowing further movement of the positioning apparatus to be prevented.

The positioning apparatus also has a rotary bearing unit to support the at least one second bearing region such that the at least one second bearing region may be rotated in relation to the at least one first bearing region. The rotary bearing unit may include a pivot joint. In one embodiment, the rotary bearing unit may be arranged between the at least one first bearing region and the at least one second bearing region.

In one embodiment, the bearing unit has a setting unit for setting an angle of inclination of the at least one second bearing region to the at least one first bearing region. This allows simple setting of the at least one second bearing region to be achieved during a change of support and/or repositioning of the patient, thereby advantageously assisting a medical operator (e.g., a physician, etc.) during the change of support and/or repositioning of the patient on a patient support apparatus (e.g., on a table of a patient support apparatus). The setting unit may, for example, include a pneumatic setting unit, an electric setting unit, a mechanical setting unit, a hydraulic setting unit, or any combination thereof. The pneumatic setting unit may include, for example, a pneumatic cylinder and/or an at least partially pneumatically driven setting element. The hydraulic setting unit may also include a hydraulic cylinder. The electric setting unit may, for example, include an electric setting element and/or an electric drive unit. The mechanical setting unit may include spring elements, for example.

In one advantageous development, the setting unit has a monitoring unit configured to control the setting of an angle of inclination of the at least one second bearing region to the at least one first bearing region as a function of a position and/or movement mode of a table of the patient support apparatus. The monitoring unit may include a sensor unit to detect the position and/or to detect the movement mode of the table of the patient support apparatus. This embodiment allows a high safety standard to be achieved for the patient on the patient support apparatus. This embodiment also advantageously allows an unwanted collision of the patient and/or the positioning apparatus with, for example, a housing enclosing a patient receiving region of a medical imaging apparatus to be prevented as the table is introduced into the patient receiving region of the medical imaging apparatus. For example, the monitoring unit may be configured such that in a movement mode and/or when the table is arranged in a position within the patient receiving region, the second bearing region is in a rest position, and movement out of this rest position is blocked. In this rest position of the second bearing region, the second bearing region is arranged at a maximum angle of essentially 180° to the first bearing region on the table, so the patient may be supported on a flat surface, which is formed by the bearing regions and a support surface of the table.

One or more of the present embodiments are based on a patient support apparatus configured, for example, to support a patient for a medical imaging examination using a medical imaging apparatus. The patient support apparatus also includes a table having a support surface to support the patient, and a positioning apparatus configured, for example, to actively assist the support and/or positioning of a patient on a patient support apparatus. The positioning apparatus includes a sliding bearing unit for movable support of the positioning apparatus on the patient support apparatus, and a bearing unit with at least two bearing regions. At least a first of the at least two bearing regions is configured to support and/or provide support on the patient support apparatus, and at least a second of the at least two bearing regions is configured to assist the positioning of the patient. The positioning apparatus (e.g., the at least one second bearing region of the bearing unit) may be used to actively assist repositioning and/or a change of support for the patient (e.g., from a sitting position to a horizontal position of the patient or from a horizontal position to a sitting position of the patient) on a patient support apparatus, thereby minimizing the force expenditure on the part of a medical operator during the change of support and/or repositioning of the patient. The sliding bearing unit may also be used to achieve advantageous positioning of the positioning apparatus on the patient support apparatus (e.g., such tailored to the size of the patient). An existing patient support apparatus may also be retrofitted in an economical manner using the positioning apparatus.

In a further embodiment of the patient support apparatus, the table has at least one sliding bearing element configured in the same way as a sliding bearing element of the patient support apparatus and configured to support the positioning apparatus such that the positioning apparatus may be moved in relation to the table in the direction of a longitudinal extension of the table. This allows simple and direct arrangement of the positioning apparatus on the patient support apparatus (e.g., the table of the patient support apparatus) to be achieved, thereby allowing the distance between the patient and a high-frequency receive unit for, for example, a magnetic resonance examination integrated within the table to be kept particularly small.

Simple introduction and/or fastening of the positioning apparatus on the table may be achieved if the at least one sliding bearing element of the table includes a slide rail. In each instance, a slide rail may be arranged on a peripheral region of the table and extends in the direction of a longitudinal extension of the table. The slide rail may, for example, include a groove-type slide rail with, for example, an L-shaped cross section, so that interference with the support surface of the table is advantageously prevented even without the positioning apparatus.

The patient support apparatus includes a monitoring unit configured to control a movement mode of the table as a function of a position of the positioning apparatus. A high safety standard may thus advantageously be achieved for the patient on the patient support apparatus. Also, an unwanted collision of the patient and/or the positioning apparatus with, for example, a housing enclosing a patient receiving region of a medical imaging apparatus may be prevented as the table is introduced into the patient receiving region of the medical imaging apparatus. For example, the monitoring unit is configured such that when the angle between the two bearing regions is smaller than 180° (e.g., smaller than 170°), the introduction of the table into a patient receiving region is blocked, so that a collision of the patient and/or the positioning apparatus with, for example, a housing enclosing a patient receiving region of a medical imaging apparatus is prevented.

In one embodiment, the patient support apparatus includes a monitoring unit configured to control a movement mode of a bearing region of the positioning apparatus as a function of a position of the table. A high safety standard may be achieved for the patient on the patient support apparatus. An unwanted collision of the patient and/or the positioning apparatus with, for example, a housing enclosing a patient receiving region of a medical imaging apparatus may also thus be prevented as the table is introduced into the patient receiving region of the medical imaging apparatus. For example, the monitoring unit may be configured such that when the table is in a movement mode and/or is arranged in a position within the patient receiving region, the second bearing region is in a rest position, and movement out of this rest position is blocked.

One or more of the present embodiments are based on a medical imaging apparatus with a patient support apparatus (e.g., configured to support a patient for a medical imaging examination using a medical imaging apparatus). The patient support apparatus includes a table having a support surface to support the patient. The patient support apparatus also includes a positioning apparatus configured, for example, to actively assist the support and/or positioning of a patient on the patient support apparatus. The positioning apparatus also includes a sliding bearing unit for movable support of the positioning apparatus on the patient support apparatus and a bearing unit with at least two bearing regions. At least a first of the at least two bearing regions is configured to support and/or provide support on the patient support apparatus, and at least a second of the at least two bearing regions is configured to assist the positioning of the patient. The positioning apparatus (e.g., the at least one second bearing region of the bearing unit) may be used to actively assist repositioning and/or a change of support for the patient (e.g., from a sitting position to a horizontal position of the patient or from a horizontal position to a sitting position of the patient) on a patient support apparatus, thereby minimizing the force expenditure on the part of a medical operator during the change of support and/or repositioning of the patient. The sliding bearing unit may also be used to achieve advantageous positioning of the positioning apparatus on the patient support apparatus (e.g., such that the positioning apparatus is tailored to the size of the patient). An existing patient support apparatus may also be retrofitted in a particularly economical manner using the positioning apparatus.

DETAILED DESCRIPTION

Figure 1:
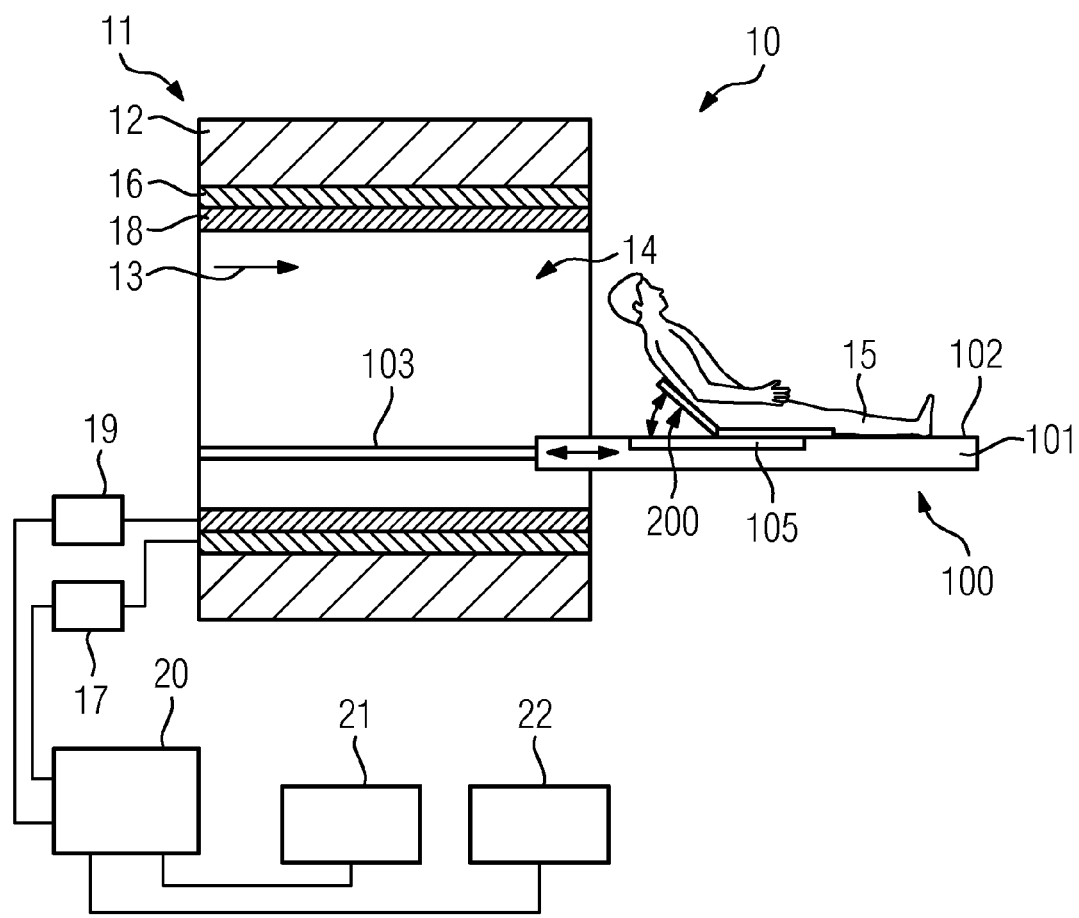
FIG. 1 shows a schematic diagram of one embodiment of a medical imaging apparatus with a patient support apparatus.

FIG. 1 shows a schematic diagram of one embodiment of a medical imaging apparatus, formed in the present exemplary embodiment by a magnetic resonance apparatus 10. Alternatively, the medical imaging apparatus may also include a computed tomography apparatus, a PET apparatus, a C-arm apparatus and/or further configurations of a medical imaging apparatus.

The magnetic resonance apparatus 10 includes a magnet unit 11 with a main magnet 12 for generating a powerful and, for example, constant main magnetic field 13. The magnetic resonance apparatus 10 also includes a patient receiving region 14 for receiving a patient 15. In the exemplary embodiment, the patient receiving region 14 is configured as cylindrical and is enclosed in a cylindrical manner in a circumferential direction by the magnet unit 11. A different configuration of the patient receiving region 14 may also be provided. The patient 15 may be moved by a patient support apparatus 100 of the magnetic resonance apparatus 10 into the patient receiving region 14.

The magnet unit 11 also includes a gradient coil unit 16 for generating magnetic field gradients, which are used for spatial encoding during imaging. The gradient coil unit 16 is controlled by a gradient control unit 17 of the magnetic resonance apparatus 10. The magnet unit 11 further includes a high-frequency antenna unit 18 and a high-frequency antenna control unit 19 for exciting a polarization, which is established in the main magnetic field 13 generated by the main magnet 12. The high-frequency antenna unit 18 is controlled by the high-frequency antenna control unit 19 and radiates high-frequency magnetic resonance sequences into an examination space that is essentially formed by the patient receiving region 14.

To control the main magnet 12 of the gradient control unit 17 and to control the high-frequency antenna control unit 19, the magnetic resonance apparatus 10 has a control unit 20 formed by a computation unit. The control unit 20 controls the magnetic resonance apparatus 10 centrally (e.g., performing a predetermined imaging gradient echo sequence). The control unit 20 also includes an evaluation unit (not shown in detail) for evaluating image data. Control information, such as imaging parameters, for example, and reconstructed magnetic resonance images may be displayed to an operator on a display unit 21 (e.g., on at least one monitor) of the magnetic resonance apparatus 10. The magnetic resonance apparatus 10 also includes an input unit 22, by which information and/or parameters may be input by an operator during a measuring operation.

To support and/or position the patient 15, the patient support apparatus 100 has a table 101 with an integrated high-frequency antenna receive unit 105 configured to detect magnetic resonance signals during a magnetic resonance examination on a patient 15. The table also has a support surface 102, on which the patient 15 is supported and/or positioned for a medical imaging examination. The support surface 102 is arranged on a surface of the high-frequency antenna receive unit 105 facing a patient region. In a head region and a foot region of the table 101, the support surface 102 of the table 102 includes, for example, further high-frequency antenna receive units (not shown in detail) and/or support pillows (not shown in detail) that are integrated in the table 101 in the regions.

The table 101 is supported in a movable manner so that a patient 15 may be introduced into the patient receiving region 14 of the magnetic resonance apparatus 10 by the table 101. The patient support apparatus 100 also has a base unit 103. The table 101 is supported such that the table 101 may be moved in relation to the base unit 103. The patient support apparatus 100 has a sliding bearing unit for movable support of the table 101 in relation to the base unit 103 (FIG. 2).

The patient support apparatus 100 further includes one embodiment of a positioning apparatus 200 that is configured to actively assist the support and/or positioning of the patient 15 on the patient support apparatus 100. The positioning apparatus 200 is arranged on the table 101 (e.g., on the support surface 102 of the table 101).

Figure 2:
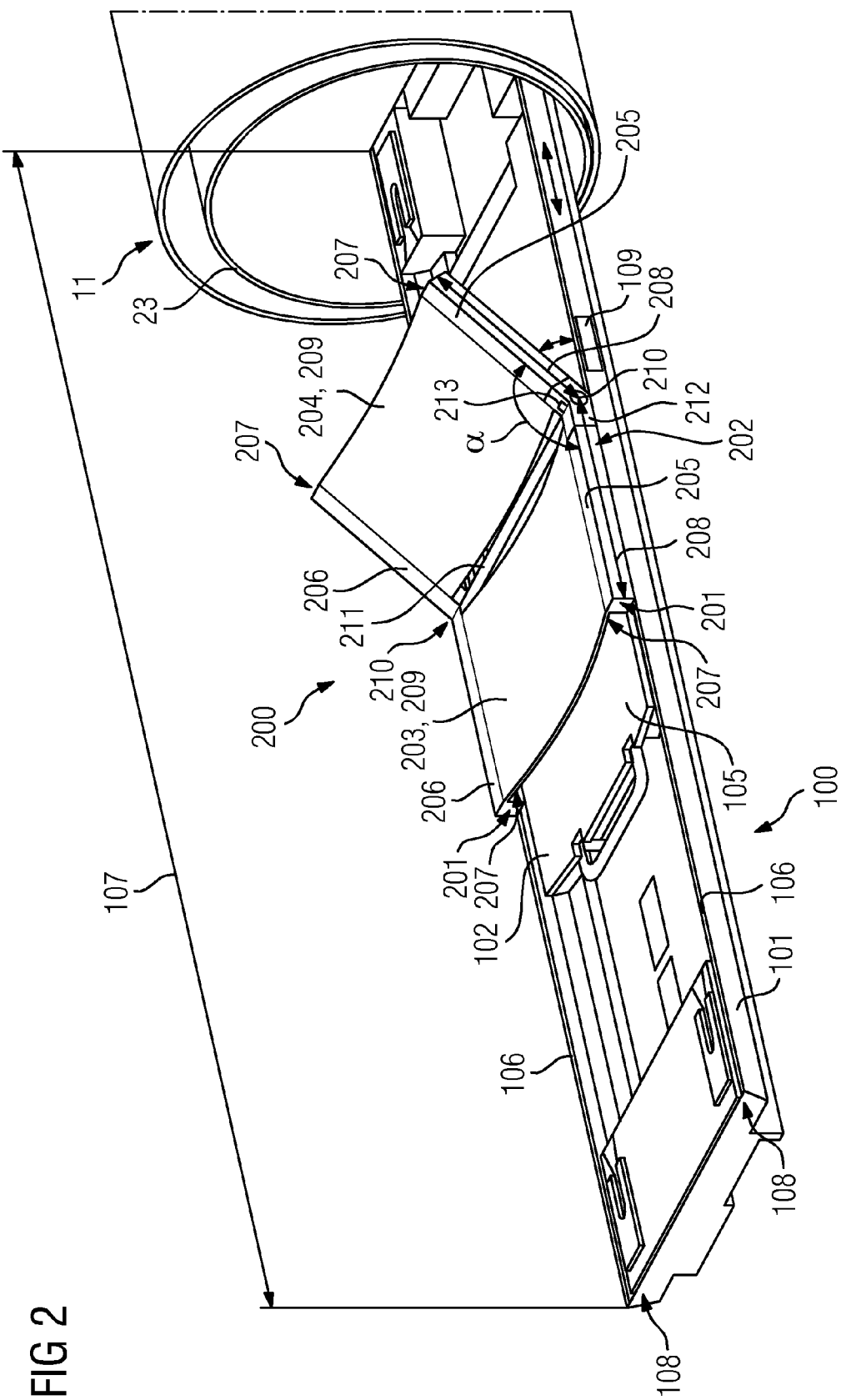
FIG. 2 shows a schematic diagram of one embodiment of the patient support apparatus with a positioning apparatus.

In FIG. 2, the table 101 of the patient support apparatus 100 is shown in more detail together with the positioning apparatus 200. The positioning apparatus 200 has a sliding bearing unit 201 configured to support the positioning apparatus 200 on the table 101 (e.g., on the support surface 102 of the table 101) in a movable manner, and a bearing unit 202 with two bearing regions 203, 204. A first of the bearing regions 203, for example, is configured to support and/or provide support for the positioning apparatus 200 on the table 101 of the patient support apparatus 100, and a second of the bearing regions 204 is configured to actively assist the positioning of the patient 15 on the patient support apparatus 100. In other embodiments, the bearing unit 202 may have more than one first bearing region 203 and/or more than one second bearing region 204.

In the present exemplary embodiment, the sliding bearing unit 201 has two sliding bearing elements (not shown in detail). Each of the two sliding bearing elements is arranged on the first bearing region 203 of the bearing unit 202. The two sliding bearing elements are each formed by slide rails. The patient support apparatus 100 (e.g., the table 101 of the patient support apparatus 100) also has two sliding bearing elements 106, which are configured in the same way as the sliding bearing elements of the positioning apparatus 200.

The sliding bearing elements 106 of the patient support apparatus 100 are each formed by a slide rail extending on the table 101 in the direction of a longitudinal extension 107 of the table 101. One of the slide rails is arranged in each instance on a laterally arranged peripheral region 108 of the table 101. In the present exemplary embodiment, the slide rails of the patient support apparatus 100 are formed by groove-type slide rails. A different configuration of the slide rails may also be provided.

The two bearing regions 203, 204 of the bearing unit 202 each have two strip elements 205, 206. One of the strip elements 205, 206 in each instance is arranged on a lateral peripheral region 207 of the respective bearing region 203, 204. The two peripheral regions 207 are also arranged on opposing sides of the bearing regions 203, 204. In the present exemplary embodiment, the strip elements 205, 206 are formed by profile strips. A strip element 205, 206 of the first bearing region 203 and a strip element 205, 206 of the second bearing region 204 are arranged on the same side of the bearing unit 202, with the two strip elements 203, 204 being arranged one behind the other in the direction of a longitudinal extension 208 of the strip elements 205, 206.

A sliding bearing element is arranged in each instance on one of the strip elements 205, 206 of the first bearing region 203. The sliding bearing elements are arranged on a region of the strip elements 205, 206 facing the table 101 of the patient support apparatus 100. The positioning apparatus 200 may be moved in the direction of the longitudinal extension 107 of the table 101 with the smallest possible amount of friction using the sliding bearing elements of the positioning apparatus 200, which are supported in the rail-type sliding bearing elements 106 of the table 101. In one embodiment, the sliding bearing unit 201 of the positioning apparatus 200 may have four or more sliding bearing elements. The individual sliding bearing elements, for example, may be arranged on end regions of the strip elements 205, 206.

The first bearing region 203 also has a securing element (not shown in detail), which secures the positioning apparatus 200 in two different spatial directions on the patient support apparatus 100 and also allows movement (e.g., a sliding movement by the sliding bearing elements in a sliding direction) that runs parallel to a longitudinal extension 207 of the table 101. The securing elements therefore secure the positioning apparatus 200 to prevent the positioning apparatus 200 falling off the table 101. The securing elements may be latching elements and/or clamping elements. However, the securing elements may be configured as a single piece and/or as a single part with the sliding bearing elements of the sliding bearing unit 201 of the positioning apparatus 200. Thus, for example, the sliding bearing elements may form a rail with an L-shaped cross section together with the securing elements. The sliding bearing elements 106 of the table 101 may also be formed by groove-type and L-shaped slide rails.

Arranged between the two strip elements 205, 206 of a respective bearing region 203, 204 in each instance is a bearing element 209 of the bearing unit. The bearing element 209 is fastened to the strip elements 205, 206. The bearing elements 209 are configured to support the patient 15. Each of the bearing elements 209 of the first bearing region 203 and the second bearing region 204 includes a flat textile structure. The flat textile structure may include a fabric and/or mesh and/or a knitted fabric, etc. In the present exemplary embodiment, the common bearing element includes a fabric formed by a material or a cloth. The bearing elements 209 also have a thickness of, for example, maximum 1 cm, 5 mm, 2.5 mm, or 1 mm, so that there is the smoothest possible transition between the table 101 (e.g., the support surface 102 of the table 101) and the bearing elements 209. The thin configuration of the bearing elements 209 also provides that the distance between the patient 15 and the high-frequency antenna receive unit 105 for a magnetic resonance examination integrated within the table 101 may be minimized so that unwanted signal attenuation as a result of the positioning apparatus 200 is advantageously prevented.

As a result of loading by the patient 15 and yielding on the part of the material and/or cloth of the bearing element 209, the bearing elements 209 formed by the material and/or cloth may rest on the table 101. When the patient 15 is supported and/or positioned on the bearing unit 202, this causes the position of the positioning apparatus 200 to be fixed in relation to the patient support apparatus 100, in that the direct contact between the bearing element 209 and the support surface 102 of the table 101 causes a friction force to act between the bearing element 209 and the support surface 102 of the table 101, preventing further movement of the positioning apparatus 200.

The positioning apparatus 200 also has two rotary bearing units 210 that are configured to support the second bearing region 204 such that the second bearing region 204 may rotate in relation to the first bearing region 203. The rotary bearing units 210 are arranged between the first bearing region 203 and the second bearing region 204 of the bearing unit 202. In the present exemplary embodiment, one of the rotary bearing units 210 is arranged in each instance between the strip elements 205, 206 of the first bearing region 203 and the second bearing region 204, which are arranged one behind the other in the direction of the longitudinal extension of the bearing unit 202. Each of the rotary bearing units 210 has a pivot joint. The first rotary bearing unit 210 and the second rotary bearing unit 210 have a common rotation axis 211. In an alternative embodiment, the rotary bearing units 210 may also have two rotation axes.

The bearing unit 202 also has a setting unit 212 for setting an angle of inclination α of the second bearing region 204 in relation to the first bearing region 203. In the present exemplary embodiment, the setting unit 212 includes an electric setting unit 212. To set the angle of inclination α of the second bearing region 204 in relation to the first bearing region 203, the electric setting unit 212 includes two electric drive units. The two electric drive units are synchronized with one another so that the same angle of inclination α is always set on both peripheral regions 207 between the two strip elements 205, 206 of the first bearing region 203 and the second bearing region 204, which are arranged one behind the other. The setting unit 212 also has a control unit (not shown in detail).

In an alternative embodiment of the setting unit 212, the setting unit 212 may also have a pneumatic setting unit, and/or a hydraulic setting unit, and/or a mechanical setting unit, and/or further setting units. The pneumatic setting unit may have, for example, a pneumatic cylinder and/or a pneumatically operated setting element (e.g., a setting arm). The hydraulic setting unit may include, for example, a hydraulic cylinder. The mechanical setting unit may include, for example, a spring element.

The electric setting units 212 are arranged in each instance between the first bearing region 203 and the second bearing region 204. One of the electric setting units 212 is arranged in each instance, for example, between a strip element 205, 206 of the first bearing region 203 and a strip element 205, 206 of the second bearing region 204. The two electric setting units 212 are, for example, arranged in a region of the rotary bearing units 210. The two electric setting units 212 are, for example, arranged on a side of the strip elements 205, 206 facing away from the bearing elements 209, so that any obstruction of the positioning of the patient 15 is prevented.

The electric setting units 212 are configured such that to set an angle of inclination α between the two bearing regions 203, 204, the two strip elements 205, 206 of the second bearing region 204 are rotated about the rotation axis 211 by the electric setting units 212 in relation to the strip elements 205, 206 of the first bearing region 203. The synchronization of the electric drive units provides that the positions of both strip elements 205, 206 of the second bearing region 204 are simultaneously changed by the same angle, so that the two strip elements 205, 206 of the second bearing region 204 are always in the same position and/or location in relation to the first bearing region 203. The setting unit 212 also has an actuation element (not shown in detail), by which an operator may start or stop the setting of the second bearing region 204 in relation to the first bearing region 203. The setting unit 212 may also have a securing element (not shown in detail) that is configured to secure a set position of the second bearing region 204. The securing element may include a mechanical securing element (e.g., a latching element and/or a clamping element).

The setting unit 212 also has a monitoring unit 213 configured to control the setting of the angle of inclination α of the second bearing region 204 in relation to the first bearing region 203 as a function of a position and/or movement mode of the table 101 of the patient support apparatus 100. The monitoring unit 213 may have a sensor unit (not shown in detail) configured, for example, to detect a position of the second bearing region 204, and an evaluation unit. The monitoring unit 213 may also be configured such that a current position of the second bearing region 204 is transmitted from the electric drive units to the monitoring unit 213 using a data transmission unit (not shown in detail). The monitoring unit 213 may also be connected via the data transmission unit to a position detection apparatus 100 (not shown in detail), so that the current position of the table 101 and/or the current movement mode of the table 101 may always be available in the monitoring unit 213.

In a rest position, the second bearing region 204 is arranged at a maximum angle of inclination α, which is essentially 180°, to the first bearing region 203 on the table 101, so that the patient 15 rests on a flat surface formed by the bearing elements 209 and the support surface 102 of the table 101. In this rest position, the monitoring unit 213 blocks movement of the second bearing region 204 while the table 101 is arranged within the patient receiving region 14 of the medical imaging apparatus, or the table 101 is in a movement mode. The monitoring apparatus 213 may thus prevent unwanted collision of the patient 15 with a housing 23 of the medical imaging apparatus enclosing the patient receiving region 14. Only when the table 101 is outside the patient receiving region 14 does the monitoring unit 213 allow any change to the position of the second bearing region 204.

The patient support apparatus 100 also has a further monitoring unit 109 configured to control a movement mode of the table 101 as a function of a position of the second bearing region 204 of the positioning apparatus 200. The further monitoring unit 109 may be connected by a data transmission unit (not shown in detail) to the sensor unit of the monitoring unit 213 of the positioning apparatus 200. The further monitoring unit 109 may also have an evaluation unit. The further monitoring unit 109 may also be connected to a position monitoring unit (not shown in detail) of the patient support apparatus 100.

For example, when the second bearing region 204 is in an active position, the second bearing region 204 is at an angle of inclination α to the first bearing region 213, which is smaller than 170°. When the second bearing region 204 is in this active position, an angle of inclination α to the first bearing region 203 is greater than, for example, 90° or 80°. In this position, the further monitoring unit 109 blocks any movement of the table 101. Only when the second bearing region 204 is arranged in the rest position does the further monitoring unit 109 allow movement of the table 101.

The monitoring unit 213, which is configured to control the setting of the angle of inclination α of the second bearing region 204 in relation to the first bearing region 203 as a function of the position and/or movement mode of the table 101, may also be part of the patient support apparatus 100. The two monitoring units 213, 109 may also be configured as a single piece and/or as a single part.

The positioning apparatus 200 (e.g., the setting of an angle of inclination α of the second bearing region 204) allows a medical operator to change support for and/or reposition the patient 15 (e.g., from a horizontal position to a sitting position or from a sitting position to a horizontal position) in a simple manner.

The positioning apparatus 200 is configured as magnetic resonance-compatible so that the positioning apparatus 200 may be used with the magnetic resonance apparatus 10.

The illustrated patient support apparatus 100 and the illustrated magnetic resonance apparatus 10 may include further components that patient support apparatuses and magnetic resonance apparatuses generally feature. The general mode of operation of a magnetic resonance apparatus and patient support apparatus is also known to the person skilled in the art, so there is no need for a detailed description of the general components here.

Although the present embodiments have been illustrated and described in detail using exemplary embodiments, the present embodiments are not limited by the disclosed examples, and other variations may be derived therefrom by the person skilled in the art without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A positioning apparatus configured to actively assist support, positioning, or support and positioning of a patient on a patient support apparatus, the positioning apparatus comprising:
   a sliding bearing unit for movable support of the positioning apparatus on the patient support apparatus; and
   a patient bearing unit comprising at least two patient bearing regions, at least a first patient bearing region of the at least two patient bearing regions being configured to support, provide support, or support and provide support on the patient support apparatus, and at least a second patient bearing region of the at least two patient bearing regions being configured to assist the positioning of the patient,
   wherein the first patient bearing region is only moveable in directions parallel to a surface of the patient support apparatus, the second patient bearing region being rotatable relative to the first patient bearing region, and
   wherein each patient bearing region of the first patient bearing region and the second patient bearing region comprises two strip elements, between which a patient bearing element of the respective patient bearing region is arranged to contact the patient and support the patient when the patient apparatus supports the patient, the patient bearing element being directly fastened to the two strip elements.

2. The positioning apparatus of claim 1, wherein the sliding bearing unit comprises at least one sliding bearing element that is arranged on the first patient bearing region.

3. The positioning apparatus of claim 2, wherein the first patient bearing region comprises at least one strip element, and the at least one sliding bearing element is arranged on the at least one strip element.

4. The positioning apparatus of claim 1, wherein the first patient bearing region comprises at least one securing element.

5. The positioning apparatus of claim 1, wherein at least one patient bearing region of the at least two patient bearing regions comprises at least one bearing element with a thickness of maximum 1 cm.

6. The positioning apparatus of claim 1, wherein at least one patient bearing region of the at least two patient bearing regions comprises at least one patient bearing element that comprises a flat textile structure.

7. The positioning apparatus of claim 1, further comprising a rotary bearing unit operable to support the second patient bearing region such that the second patient bearing region is rotatable in relation to the first patient bearing region.

8. The positioning apparatus of claim 7, wherein the rotary bearing unit is arranged between the first patient bearing region and the second patient bearing region.

9. The positioning apparatus of claim 1, wherein the patient bearing unit comprises a setting unit operable to set an angle of inclination of the second patient bearing region in relation to the first patient bearing region.

10. The positioning apparatus of claim 9, wherein the setting unit comprises a monitoring unit configured to control a setting of the angle of inclination of the second patient bearing region in relation to the first patient bearing region as a function of a position mode, a movement mode, or a position and movement mode of a table of the patient support apparatus.

11. The positioning apparatus of claim 1, wherein the at least one patient bearing region comprises the second patient bearing region.

12. The positioning apparatus of claim 1, wherein a bearing element of the first patient bearing region is made of a flexible material.

13. The positioning apparatus of claim 1, further comprising:
   at least two setting units configured to set an angle of inclination of the second patient bearing region in relation to the first patient bearing region.

14. A patient support apparatus configured to support a patient for a medical imaging examination using a medical imaging apparatus, the patient support apparatus comprising:
   a table comprising a support surface to support the patient; and
   a positioning apparatus configured to actively assist support, positioning, or support and positioning of the patient on the patient support apparatus, the positioning apparatus comprising:
   a sliding bearing unit for movable support of the positioning apparatus on the patient support apparatus; and
   a patient bearing unit comprising at least two patient bearing regions, at least a first patient bearing region of the at least two patient bearing regions being configured to support, provide support, or support and provide support on the patient support apparatus, and at least a second patient bearing region of the at least two patient bearing regions being configured to assist the positioning of the patient,
   wherein the first patient bearing region is only moveable in directions parallel to a surface of the patient support apparatus, the second patient bearing region being rotatable relative to the first patient bearing region, and
   wherein the at least two patient bearing regions comprise two strip elements, between which a patient bearing element of the at least two patient bearing regions is arranged to contact the patient and support the patient when the patient support apparatus supports the patient, the patient bearing element being directly fastened to the two strip elements.

15. The patient support apparatus of claim 14, wherein the table comprises at least one sliding bearing element configured in the same way as a sliding bearing element of the positioning apparatus and is configured to support the positioning apparatus such that the positioning apparatus is movable in relation to the table in a direction of a longitudinal extension of the table.

16. The patient support apparatus of claim 15, wherein the sliding bearing element of the table comprises a slide rail.

17. The patient support apparatus of claim 14, further comprising a monitoring unit configured to control a movement mode of the table as a function of a position of the positioning apparatus.

18. The patient support apparatus of claim 14, further comprising a monitoring unit configured to control a movement mode of a patient bearing region of the at least two patient bearing regions of the positioning apparatus as a function of a position of the table.

19. A medical imaging apparatus comprising:
a patient support apparatus configured to support a patient for a medical imaging examination using a medical imaging apparatus, the patient support apparatus comprising:
  a table comprising a support surface to support the patient; and
  a positioning apparatus configured to actively assist support, positioning, or support and positioning of the patient on the patient support apparatus, the positioning apparatus comprising:
    a sliding bearing unit for movable support of the positioning apparatus on the patient support apparatus; and
    a patient bearing unit comprising at least two patient bearing regions in contact with the patient when the patient support apparatus supports the patient, at least a first patient bearing region of the at least two patient bearing regions being configured to support, provide support, or support and provide support on the patient support apparatus, and at least a second patient bearing region of the at least two patient bearing regions being configured to assist the positioning of the patient,
  wherein the first patient bearing region is only moveable in directions parallel to a surface of the patient support apparatus, the second patient bearing region being rotatable relative to the first bearing region, and
  wherein at least one patient bearing region of the at least two patient bearing regions comprises two strip elements, between which a patient bearing element of the at least one patient bearing region is arranged to support the patient, the patient bearing element being directly fastened to the two strip elements.

20. The medical imaging apparatus of claim 19, wherein the sliding bearing unit comprises at least one sliding bearing element that is arranged on the first patient bearing region.

21. The medical imaging apparatus of claim 20, wherein the first patient bearing region comprises at least one strip element, and the at least one sliding bearing element is arranged on the at least one strip element.

22. The medical imaging apparatus of claim 19, wherein the first patient bearing region comprises at least one securing element.

* * * * *